(12) United States Patent
Betancourt et al.

(10) Patent No.: US 10,449,150 B2
(45) Date of Patent: Oct. 22, 2019

(54) FLUIDIC SYSTEM FOR HIGH THROUGHPUT PREPARATION OF MICROPARTICLES AND NANOPARTICLES

(71) Applicant: Texas State University, San Marcos, TX (US)

(72) Inventors: Tania Betancourt, San Marcos, TX (US); John L. Massingill, Jr., San Marcos, TX (US); Holly Stretz, San Marcos, TX (US)

(73) Assignee: Texas State University, San Marcos, TX (US)

( * ) Notice: Subject to any disclaimer, the term of this patent is extended or adjusted under 35 U.S.C. 154(b) by 407 days.

(21) Appl. No.: 15/312,569

(22) PCT Filed: May 20, 2014

(86) PCT No.: PCT/US2014/038757
§ 371 (c)(1),
(2) Date: Nov. 18, 2016

(87) PCT Pub. No.: WO2015/178892
PCT Pub. Date: Nov. 26, 2015

(65) Prior Publication Data
US 2017/0119670 A1 May 4, 2017

(51) Int. Cl.
*B01J 14/00* (2006.01)
*A61K 9/16* (2006.01)
(Continued)

(52) U.S. Cl.
CPC .............. *A61K 9/16* (2013.01); *A61K 9/1682* (2013.01); *A61K 49/0004* (2013.01);
(Continued)

(58) Field of Classification Search
None
See application file for complete search history.

(56) References Cited

U.S. PATENT DOCUMENTS

| | | | |
|---|---|---|---|
| 3,758,404 A * | 9/1973 | Clonts ................ | B01D 11/0449 208/263 |
| 6,471,995 B1 * | 10/2002 | Ramstack ............ | A61K 9/1647 264/4 |

(Continued)

FOREIGN PATENT DOCUMENTS

WO   WO-2013177057 A1 * 11/2013 .............. B01J 14/00

OTHER PUBLICATIONS

Jamkhindikar et al (High throughput fiber reactor process for organic nanoparticle production: Poly(N-isopropylacrylamide), polyacrylamide, and alginate, J. Appl. Polym. Sci. 2017 45524) (Year: 2017).*

*Primary Examiner* — Rachel Kahn
(74) *Attorney, Agent, or Firm* — Meyertons, Hood, Kivlin, Kowert & Goetzel, P.C.

(57) ABSTRACT

A fiber fluidic system may be used to produce particles (e.g., NPs and/or microparticles). The fiber fluidic system may include a cylinder with a plurality of elongated fibers oriented along a length of the cylinder. The cylinder may have a first opening at or near a first end of the cylinder and a second opening downstream of the first opening. A constrained phase fluid may be provided through the first opening and a free phase fluid may be provided through the second opening to produce particles (e.g., NPs and/or microparticles) through a second end of the cylinder. The fiber fluidic system may be used to continuously produce the particles at high throughput.

16 Claims, 2 Drawing Sheets

(51) Int. Cl.
  *B01J 13/02* (2006.01)
  *B01J 13/14* (2006.01)
  *A61K 49/00* (2006.01)
  *C09B 67/02* (2006.01)
  *G01N 33/58* (2006.01)

(52) U.S. Cl.
  CPC ............... *B01J 13/02* (2013.01); *B01J 13/14* (2013.01); *C09B 67/0097* (2013.01); *G01N 33/585* (2013.01); *G01N 33/587* (2013.01)

(56) References Cited

U.S. PATENT DOCUMENTS

| | | |
|---|---|---|
| 7,618,544 B2 | 11/2009 | Massingill, Jr. |
| 8,128,825 B2 | 3/2012 | Massingill |
| 9,168,469 B2 | 10/2015 | Massingill |
| 9,468,866 B2 | 10/2016 | Massingill |
| 9,815,001 B2 | 11/2017 | Massingill |
| 10,189,806 B2 | 1/2019 | Massingill |
| 2015/0315618 A1 | 11/2015 | Massingill |

* cited by examiner

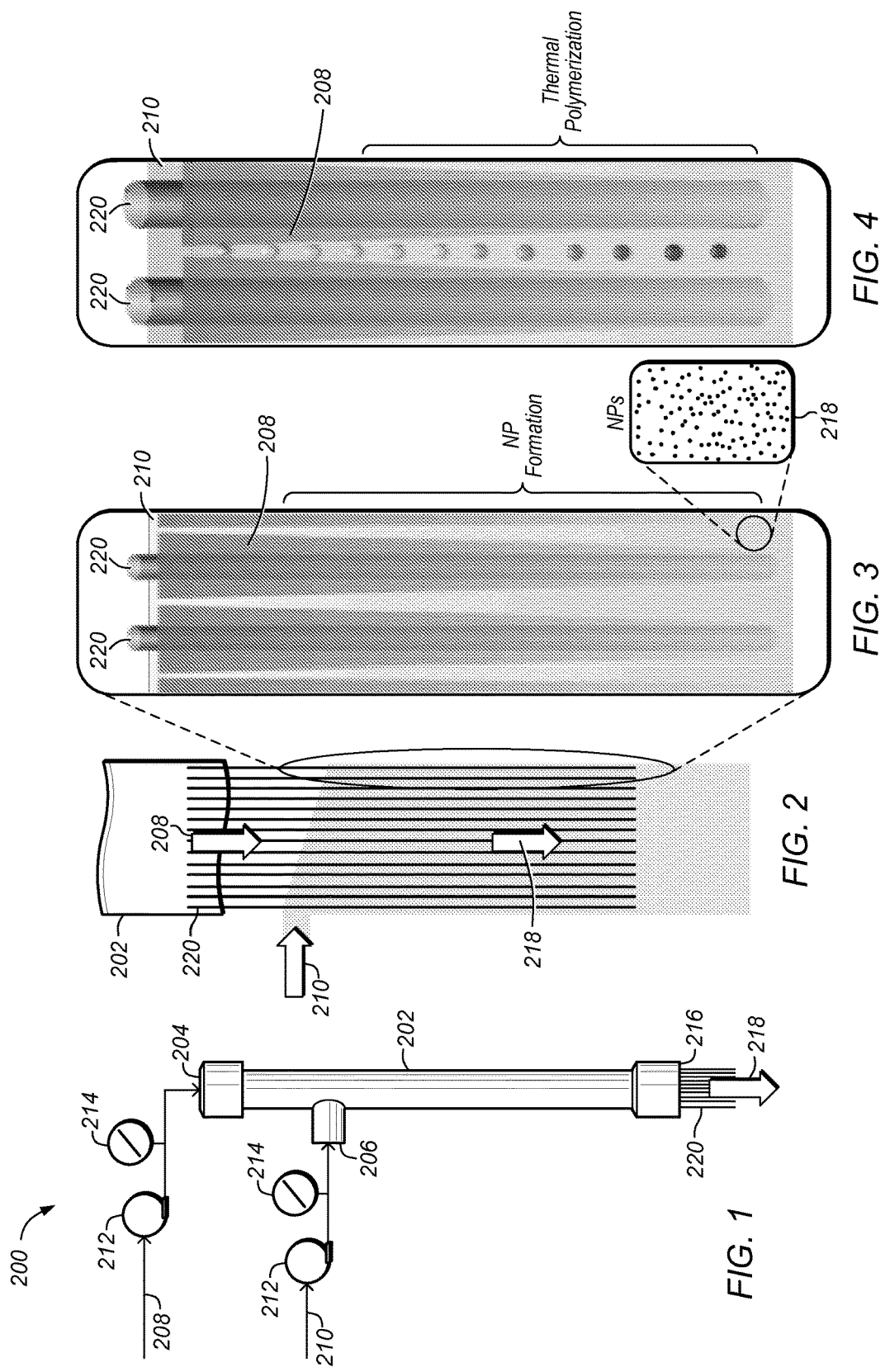

FLUIDIC SYSTEM FOR HIGH THROUGHPUT PREPARATION OF MICROPARTICLES AND NANOPARTICLES

BACKGROUND

1. Field of the Invention

The present invention relates to a system and process for producing particles such as nanoparticles. More particularly, the invention relates to a continuous process for producing monodispersed microparticles and/or nanoparticles using a fiber fluidic system.

2. Description of Related Art

Nanoparticles (NPs) are insoluble materials that can range in size from about 1 nm to about 100 nm. In some cases, NPs may have a size that ranges from about 5 nm to about 1 µm. The small size and high surface area of NPs make them highly suitable for certain biomedical applications. The small size of NPs gives them the ability to be injected locally or systemically, extravasate into diseased tissues, enter cells, and interact with targets at the molecular level; providing a range of useful biomedical opportunities. The high surface area of NPs enables faster and stronger interaction with targets than with macro-scaled counterparts. Additionally, the macromolecular size of NPs allows them to act as carriers for the delivery of high payloads of drugs or contrast agents. NPs also allow surface functionalization with ligands that overcome physiological barriers and provide targeting ability. With such properties, it is understood that NP-based technologies may have the potential to enable the development of new diagnostic, therapeutic, and theranostic technologies that offer higher efficacy, bioavailability, individualization, and safety compared to current technologies.

Currently, there have been only a few NP-based systems used as therapeutic or biotechnological tools. It is expected, however, that nanotechnology will play an increasing role in health care and biomedicine in the near future. FDA-approved NP-based therapeutics currently include liposomal formulations of doxorubicin (Doxil®), daunorubicin (DaunoXome®), and amphotericin B (Abelcet®, Amphotec®, and AmBisome®), as well as albumin-based protein NPs for paclitaxel delivery (Abraxane®). Despite the high versatility and long history of polymeric materials in medicine, to date no polymeric NP-based therapeutic systems have been commercialized. There are, however, currently many ongoing clinical trials involving NPs, many of which are related to cancer therapeutics.

In the area of diagnostics, polymeric NPs have applications as contrast agents for in vivo, ex vivo, or in vitro biomarker/pathogen detection and imaging. NPs may also have applications as capture agents for the separation of biomolecules. NPs may also be incorporated into nanocomposites or coatings in medical devices (including drug eluting stents, tissue engineered scaffolds, or antibacterial coatings) that require controlled release of active agents, nanotexturing, or high porosity for enhanced physiological interaction and response.

In the area of biotechnology, polymeric NPs may also have significant applications in bioseparations. NPs may be used as templates for preparation of porous media for the separation of biomolecules via electrophoresis. In these materials, stimuli-responsive NPs may provide tunable porosity. In such applications, NP monodispersity may be critical for analytical reproducibility.

Two main approaches have been typically used for the preparation of NPs. Top-down approaches such as wet milling utilize mechanical work to create small particles from larger materials. In contrast, bottom-up approaches (such as polymerization, emulsification, or precipitation) result in the formation of NPs by assembly of smaller building blocks. Forming NPs by such methods enables greater control over the resulting architecture and properties of the NP. In the bottom-up method, NPs are typically prepared by the introduction of a precursor phase (monomers or polymers) into a second continuous phase in the form of a dispersion or emulsion. NP formation then may occur through the precipitation, gelation, or polymerization of the precursors. Encapsulation of active agents is carried out by inclusion of said agent within the polymer-rich phase, which results in the entrapment of the agent upon NP solidification.

While such synthetic methods have been widely used at the laboratory scale, scale-up issues for commercialization have been common due to the difficulty in providing homogenous mixing in bulk processes, which leads to highly polydispersed (inhomogeneous) NP populations. In addition, these methods may require very high energy mixing that can prevent their use for the encapsulation of labile active agents such as protein therapeutics. The monodispersity of NP suspensions plays a key role in the effectiveness of NPs in a number of applications, including biomedicine. Although laboratory processes for reproducible synthesis of polymeric particles (e.g., NPs) through emulsion and nano-precipitation methods have matured, the development of suitable methods for synthesis of monodispersed NPs on the scales required for commercialization has not yet been achieved. Thus, it is important to develop new processes that could enable the reproducible preparation of NPs on a large scale.

Fiber Film® Contactors (FCCs) were first introduced by Merichem Company (Houston, Tex., U.S.A.) as an improved method for caustic washing of petroleum that avoids the formation of emulsions. The contactor in an FCC can be filled with 8 µm to 120 µm diameter fibers that are oriented along the length of the pipe. A fiberphilic phase is first introduced to the FCC, which forms a constrained film around the fibers driven by polarity and surface tension. Typically, a 0.25 µm to 4 µm thick aqueous phase forms a sheath around hydrophilic fibers. Next, a free phase is introduced downstream and forced to flow in between the coated fibers. In extraction processes, the two phases are immiscible, which results in a filming process that creates a large interfacial surface area. This surface area is continuously renewed for highly efficient extraction. The fact that an emulsion is never formed is beneficial as immediate phase separation can occur upon exit from the FCC.

SUMMARY

In certain embodiments, a system for forming particles includes a fiber fluidic system. The fiber fluidic system may include a cylinder with a plurality of elongated fibers oriented along a length of the cylinder. The cylinder may include a first opening and a second opening at or near a first end (e.g., a top end or an entrance) of the cylinder. A constrained phase fluid may be provided through the first opening and a free phase fluid may be provided through the second opening during use to produce particles through a second end (e.g., a bottom end or an exit) of the cylinder. The particles may range in size between about 1 nm and about 100 µm.

In certain embodiments, a method for forming particles includes providing a constrained phase fluid into a cylinder at or near the first end of the cylinder. The cylinder may include a plurality of elongated fibers oriented along a length of the cylinder. The elongated fibers may be wetted with the constrained phase fluid. A free phase fluid may be provided into the cylinder. The free phase fluid may flow in a void space between the wetted elongated fibers. Particles may be formed along a length of the wetted elongated fibers. The particles may be produced at or near the second end of the cylinder. The particles may range in size between about 1 nm and about 100 µm.

In some embodiments, the particles are monodispersed particles. The particles may range in size between about 5 nm and about 2.5 µm. The elongated fibers may include hydrophilic fibers or hydrophobic fibers. In some embodiments, the constrained phase fluid is an aqueous solution and the free phase fluid is a precursor solution with polymer or monomer molecules in a free phase solution. In some embodiments, the free phase fluid is an aqueous solution and the constrained phase fluid is a precursor solution with polymer or monomer molecules in a constrained phase solution. In some embodiments, the constrained phase fluid and the precursor fluid are provided continuously through the openings in the cylinder to continuously produce particles.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 1 depicts a schematic representation of an embodiment of a fiber fluidic system.

FIG. 2 depicts a schematic representation of an embodiment of the inside of a cylinder.

FIG. 3 depicts a schematic of an embodiment of an enlarged section of a cylinder showing a nanoprecipitation process.

FIG. 4 depicts a schematic of an embodiment of an enlarged section of a cylinder showing an emulsion process.

Figure 5:
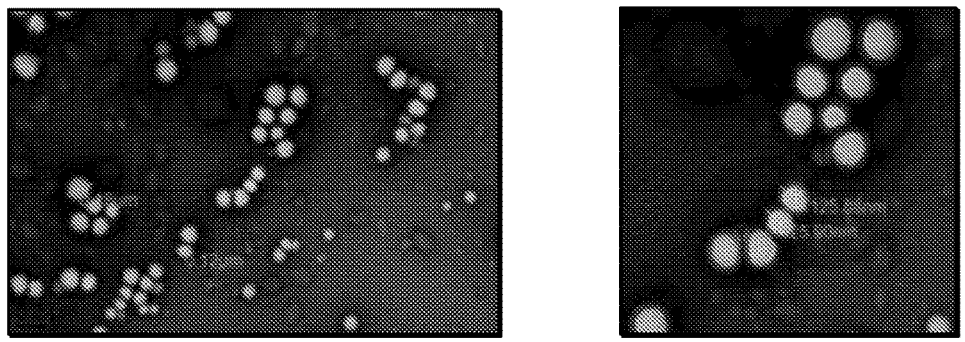
FIG. 5 shows electron microscopy images of poly(lactide-co-glycolide) (PLGA) NPs produced in an example.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

In the context of this patent, the term "nanoparticles" (NPs) refers to particles with a size that ranges from about 1 nm to about 100 nm. The term "microparticles" refers to particles with a size that ranges from about 100 nm to 100 µm.

In certain embodiments, a fiber fluidic system (similar to an FCC system) is used to produce nanoparticles (NPs) (e.g., monodispersed NPs) and/or microparticles. In certain embodiments, the fiber fluid system produces particles substantially continuously. FIG. 1 depicts a schematic representation of an embodiment of a fiber fluidic system. In certain embodiments, fiber fluidic system 200 includes cylinder 202. Cylinder 202 may include first opening 204 at or near a first end (e.g., a top end or entrance) of the cylinder and second opening 206 downstream (below) the first opening. Second opening 206 may be located on cylinder 202 slightly downstream from first opening 202 (e.g., the second opening is positioned in the upper half of the cylinder).

In certain embodiments, first fluid 208 is provided to cylinder 202 through first opening 204 and second fluid 210 is provided to the cylinder through second opening 206. Pumps 212 may be used to move (pump) the fluids into cylinder 202. Gauges 214 may be used to assess (monitor) the flow of fluids into cylinder 202.

In certain embodiments, cylinder 202 includes third opening 216 at or near a second end (e.g., a bottom end or exit) of the cylinder. Third opening 216 may allow third fluid 220 to be output from cylinder 202. In certain embodiments, third opening 216 is fully downstream of first opening 204 (e.g., the first opening is at one end of the cylinder and the third opening is at the other end of the cylinder).

FIG. 2 depicts a schematic representation of an embodiment of the inside of cylinder 202. In certain embodiments, fibers 220 are oriented along a length of cylinder 202. In certain embodiments, fibers 220 extend along substantially the length of cylinder 202 between first opening 204 and third opening 216. Fibers 220 may be, for example, elongated fibers. In certain embodiments, fibers 220 are hollow fibers. In certain embodiments, fibers 220 are hydrophilic fibers. In certain embodiments, fibers 220 are hydrophobic fibers. In certain embodiments, fibers 220 are fibers with a diameter between about 8 µm and about 12 µm. Fibers 220 may, however, have other diameters as needed to produce desired NPs.

As shown in FIGS. 1 and 2, first fluid 208 enters cylinder 202 and flows along the length of fibers 220. In certain embodiments, first fluid 208 is a constrained phase fluid. In some embodiments, first fluid 208 is an aqueous solution. As first fluid 208 flows along fibers 220, the first fluid wets the fibers and forms a thin film around the fibers.

While fibers 220 are wetted with first fluid 208, second fluid 210 is provided into cylinder 202 downstream of the first fluid and flows towards third opening 216. In certain embodiments, second fluid 210 is a free phase fluid. In some embodiments, second fluid 210 is a precursor solution. The precursor solution may include polymer and/or monomer molecules in a free phase solution. Second fluid 210 may flow in a void space between fibers 220 in cylinder 202.

In some embodiments, first fluid 208 is the precursor solution and second fluid 210 is the aqueous solution. In such embodiments, the precursor solution (e.g., first fluid 208) is the constrained phase fluid that wets the fibers and the aqueous solution (e.g., second fluid 210) is the free phase fluid. In such embodiments, the precursor solution includes polymer and/or monomer in a constrained phase solution. In some embodiments, processes using the precursor solution as first fluid 208 and the aqueous solution as second fluid 210 utilize hydrophobic fibers as fibers 220.

First fluid 208 and second fluid 210 may be immiscible inside cylinder 202 and the fluids may rapidly mix inside the cylinder along fibers 220. The immiscibility of the fluids results in a filming process that creates a large interfacial surface area along fibers 220. Third fluid 218 may be formed as first fluid 208 and second fluid 210 move along fibers 220.

In certain embodiments, third fluid 218 includes particles (e.g., nanoparticles (NPs) and/or microparticles) that fall out of the immiscible solution of first fluid 208 and second fluid 210 at the aqueous (wetted) surface of fibers 220. For example, the particles may be held in solution in third fluid 218. In certain embodiments, third fluid 218 includes particles in a precipitated suspension (e.g., the particles are monodispersed particles such as monodispersed NPs). The particles (e.g., NPs and/or microparticles) in third fluid 218 may be, for example, polymeric particles, non-polymeric particles, and/or inorganic particles. Third fluid 218 may then be removed from cylinder 202 through third opening 216.

In some embodiments, particles (e.g., NPs and/or microparticles) are formed in third fluid 218 through a nanoprecipitation process inside cylinder 202. FIG. 3 depicts a schematic of an embodiment of enlarged section 202A of cylinder 202 showing a nanoprecipitation process. In the nanoprecipitation process, first fluid 208 wets fibers 220 such that hydrodynamic flow focusing of second fluid 210 occurs in the void spaces between the fibers. As shown in FIG. 3, second fluid 210 rapidly mixes with first fluid 208, which is flowing faster than the second fluid. During the process, the fluids rapidly mix through diffusion and consequently precipitate particles. The particles may precipitate due to nucleation and/or nanoparticle growth through further polymer aggregation. In certain embodiments of the nanoprecipitation process, second fluid 210 includes hydrophobic copolymers and/or amphiphilic block-copolymers.

In some embodiments, particles (e.g., NPs and/or microparticles) are formed in third fluid 218 through an emulsion process or an emulsion polymerization process inside cylinder 202. FIG. 4 depicts a schematic of an embodiment of enlarged section 202A of cylinder 202 showing an emulsion process. In the emulsion process, polymers within second fluid 210 break up into droplets 222 due to hydrodynamic instability. Droplets 222 may then form particles through polymerization/cross-linking (e.g., thermal polymerization/cross-linking) of the precursors in second fluid 210 and/or evaporation of solvent.

In certain embodiments, first fluid 208 and second fluid 210 are continuously provided to cylinder 202, as shown in FIGS. 1 and 2. Thus, third fluid 218 may be continuously produced from cylinder 202 and a particle suspension is continuously produced from system 200. In certain embodiments, system 200 may be scaled linearly to continuously produce large quantities of particles (e.g., NPs and/or microparticles). For example, system 200 may be scaled up by increasing the diameter of the overall system while maintaining fiber packing density to increase production rates. In some embodiments, system 200 is scaled to produce hundred gram quantities of particles per day using continuous flow through cylinder 202. Such production quantities are much higher than those obtained using current batch production methods. Thus, system 200 provides a more economical and efficient method for production of particles (e.g., NPs and/or microparticles) than current batch production methods.

Figure 7:
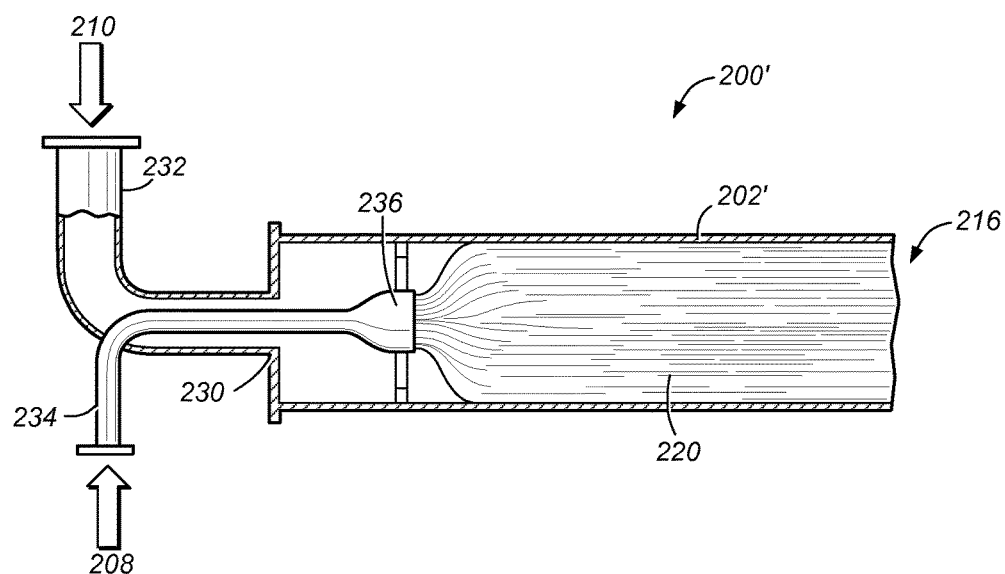
FIG. 7 depicts a schematic representation of another embodiment of a fiber fluidic system.

FIG. 7 depicts a schematic representation of another embodiment of a fiber fluidic system. System 200' may include cylinder 202'. Cylinder 202' may include opening 230 at or near a first end of the cylinder. Opening 230 may be coupled to first conduit 232. Second conduit 234 may enter cylinder 202' at or near the first end of the cylinder. In certain embodiments, as shown in FIG. 7, second conduit 234 enters first conduit 232 through a wall of the first conduit and is positioned inside the first conduit before extending inside cylinder 202'. In some embodiments, second conduit 234 enters cylinder 202' through another opening in the cylinder. Cylinder 202' may include third opening 216 at or near a second end of the cylinder.

In certain embodiments, conduit 234 is coupled to fluid distribution unit 236. Fluid dispersion unit 236 may, for example, be a fluid distribution means or a perforated node. An example of a fluid distribution means is provided in U.S. Pat. No. 3,992,156 to Clonts. Fluid dispersion unit 236 may be coupled to fibers 220, which are oriented along a length of cylinder 202'. Fibers 220 may extend along a substantial length of cylinder 202' between fluid dispersion unit 236 and third opening 216.

In certain embodiments, first fluid 208 is provided to cylinder 202' through conduit 234 and second fluid 210 is provided to the cylinder through conduit 232. Third fluid 220 may be output from cylinder 202' at third opening 216. As shown in FIG. 7, first fluid 208 enters cylinder 202' through fluid distribution unit 236 and flows along the length of fibers 220. As first fluid 208 flows along fibers 220, the first fluid wets the fibers and forms a thin film around the fibers.

While fibers 220 are wetted with first fluid 208, second fluid 210 is provided into cylinder 202' upstream of the first fluid through conduit 232 and flows towards third opening 216. Third fluid 218 may be formed as first fluid 208 and second fluid 210 move along fibers 220, substantially similar to the formation of the third fluid in system 200, depicted in FIGS. 1-4. Thus, system 200' may produce third fluid 218 that includes NPs, such as monodispersed NPs, in a precipitated suspension. Third fluid 218 may then be removed from cylinder 202 through third opening 216.

In certain embodiments, system 200 and/or system 200' allow high degrees of control over particle size. Particle size may be controlled by controlling the rate and geometry in which the interaction between the distinct phases (e.g., first fluid 208 and second fluid 210) takes place. The particles produced from system 200 and/or system 200' may have a range of sizes or be constrained to a range of sizes depending on selected factors in the system. Factors in system 200 and/or system 200' that may be used to control particle size include, but are not limited to, fluid flow rates (e.g., flow rates of first fluid 208 and/or second fluid 210), precursor concentrations in the distinct phases, fiber diameter, and/or fiber packing. These factors may be adjusted to provide a desired and/or optimized particle size.

In certain embodiments, system 200 and/or system 200' produce particles in third fluid 218. In certain embodiments, particles in third fluid 218 include particles that range in size between about 1 nm and about 100 μm (e.g., the particles include microparticles and nanoparticles). In some embodiments, particles in third fluid 218 include particles that range in size between about 1 nm and about 2.5 μm (e.g., the particles include microparticles and nanoparticles). In some embodiments, particles in third fluid 218 include particles that range in size between about 1 nm and about 100 nm (e.g., the particles include nanoparticles). In some embodiments, particles in third fluid 218 include particles that range between about 1 nm and about 500 nm, between about 1 nm and about 1 μm, or between about 5 nm and about 2.5 μm.

In some embodiments, the process for forming particles in system 200 and/or system 200' may be adjusted to produce particles using many different varieties of polymer and monomer precursors provided in second fluid 210. For example, system 200 and/or system 200' may be used to produce hydrophobic, core-shell, and/or hydrogel-type particles (e.g., NPs and/or microparticles) using different varieties of polymer and monomer precursors. In some embodiments, system 200 and/or system 200' provide high throughput production of temperature responsive particles (e.g., NPs). Temperature responsive particles may be useful in bioseparations, drug delivery, and biosensing.

In some embodiments, system 200, or system 200', has a relatively small footprint. The footprint of system 200 and/or system 200' may be smaller than the footprint of current batch reactors used for nanoparticle production. In addition, system 200 and/or system 200' may be easily integrated into current production systems.

System 200 and/or system 200' may also reduce or eliminate the need for moving parts in the production of particles. For example, system 200 and/or system 200' may eliminate the need for high energy mixing, homogenization, and/or sonication. Thus, system 200 and/or system 200' may save energy and reduce potential downtime associated with mechanical problems.

Particles (e.g., nanoparticles (NPs) and/or microparticles) produced by system 200 and/or system 200' may be used in a variety of applications. For example, particles produced by system 200 and/or system 200' may be used in biomedicine. Examples of uses of particles in biomedicine include, but are not limited to, drug delivery, contrast agents for bioimaging, fluorescent tags for microscopy and cellular labeling, photothermal ablation of tumors, photodynamic therapy, fillers for nanocomposites, and bioseparation processes.

In addition, particles produced by system 200 and/or system 200' may be used in many other applications. Particles produced by system 200 and/or system 200' may be organic, inorganic, and/or hybrid polymeric particles that are useful in other applications. In certain embodiments, particles produced by system 200 and/or system 200' are used in latex paints (e.g., latex particles), as pigments, or as inks. In some embodiments, particles are used as fine fertilizer particles (e.g., less than about 100 µm). In some embodiments, particles produced by system 200 and/or system 200' are metal catalyst particles or other catalyst particles. Metal catalyst particles may include, for example, silver particles, gold particles, platinum particles, palladium particles, and combinations thereof.

EXAMPLES

Example 1

A preliminary run for preparation of poly(lactic-co-glycolic acid) (PLGA) NPs with a laboratory-sized prototype yielded NPs ranging between about 125 nm and about 180 nm in diameter (e.g., about 175 nm in diameter) with a polydispersity (PDI) of 0.134. These NPs were produced at a relatively conservative rate of 9 g/hr, which could be increased with further experimentation/design. FIG. 5 shows electron microscopy images of these NPs. In contrast, bulk batch synthesis of NPs in the laboratory produced much higher PDI polymer suspensions.

Example 2

Figure 6:
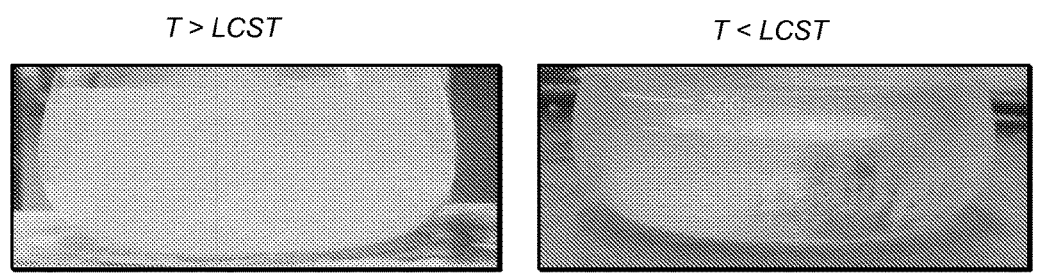
FIG. 6 depicts images of poly(N-isopropyl acrylamide) (PNIPAAm) NPs produced in an example.

Initial trial runs for the preparation of poly(N-isopropyl acrylamide) (PNIPAAm) thermoresponsive NPs yielded 41.7 nm NPs with a PDI of 0.15. The reactor was operated at 80° C. with a production rate of 25 g/hr and included a recycle loop. The resultant NPs actively showed a lower critical solution temperature (LCST) in water at 32° C. FIG. 6 depicts images of PNIPAAm NPs above LCST (left) and below LCST (right). The images in FIG. 6 demonstrate the ability of the fiber fluidic system (e.g., system 200 described above) to enable large scale synthesis of thermally responsive NPs. Further refinement may allow for identification of more optimal reactor conditions. For example, the addition of internal chemical initiation within the reactor chemistry may provide improved reactor conditions. In contrast, bulk batch synthesis of the same PNIPAAm in the laboratory produced 100-300 nm NPs with a PDI of 0.45.

It is to be understood the invention is not limited to particular systems described which may, of course, vary. It is also to be understood that the terminology used herein is for the purpose of describing particular embodiments only, and is not intended to be limiting. As used in this specification, the singular forms "a", "an" and "the" include plural referents unless the content clearly indicates otherwise. Thus, for example, reference to "a device" includes a combination of two or more devices and reference to "a material" includes mixtures of materials.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for forming particles, comprising:
providing a constrained phase fluid into a cylinder at or near a first end of the cylinder, wherein the cylinder comprises a plurality of elongated fibers oriented along a length of the cylinder;
wetting the elongated fibers with the constrained phase fluid;
providing a free phase fluid into the cylinder, wherein the free phase fluid flows in a void space between the wetted elongated fibers;
forming particles along a length of the wetted elongated fibers, wherein the particles range in size between about 1 nm and about 100 µm; and
producing the particles at or near a second end of the cylinder.

2. The method of claim 1, wherein the produced particles comprise monodispersed particles.

3. The method of claim 1, wherein the produced particles range in size between about 5 nm and about 2.5 µm.

4. The method of claim 1, wherein the constrained phase fluid comprises an aqueous solution and the free phase fluid comprises a precursor solution.

5. The method of claim 4, wherein the precursor solution comprises polymer or monomer molecules in a free phase solution.

6. The method of claim 1, wherein the constrained phase fluid comprises a precursor solution and the free phase fluid comprises an aqueous solution.

7. The method of claim 6, wherein the precursor solution comprises polymer or monomer molecules in a constrained phase solution.

8. The method of claim 1, wherein the free phase fluid is provided downstream of the first end of the cylinder.

9. The method of claim 1, further comprising continuously providing the constrained phase fluid and the free phase fluid into the cylinder.

10. The method of claim 1, further comprising adjusting a flow rate of the constrained phase fluid and/or a flow rate of the free phase fluid to select a desired particle size.

11. The method of claim 1, wherein the elongated fibers comprise hydrophilic fibers or hydrophobic fibers.

12. The method of claim 1, wherein the elongated fibers comprise hollow fibers.

13. The method of claim 1, wherein the constrained phase fluid and the free phase fluid form a solution in the cylinder.

14. The method of claim 13, wherein forming the particles comprises forming particles in the solution at the wetted elongated fibers.

15. The method of claim 1, further comprising selecting a diameter of the elongated fibers to determine a size of the produced particles.

16. The method of claim 1, further comprising selecting a packing of the elongated fibers to determine a size of the produced particles.

\* \* \* \* \*